United States Patent
Curless et al.

(10) Patent No.: US 7,118,884 B1
(45) Date of Patent: Oct. 10, 2006

(54) METHOD FOR CONTROLLING METALLOPHOSPHATE PRECIPITATION IN HIGH CELL DENSITY FERMENTATIONS

(75) Inventors: Craig Eric Curless, Moorpark, CA (US); Jeffrey Burke Baclaski, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 1822 days.

(21) Appl. No.: 08/701,032

(22) Filed: Aug. 21, 1996

Related U.S. Application Data

(63) Continuation of application No. 08/235,573, filed on Apr. 28, 1994, now abandoned.

(51) Int. Cl.
C07K 21/06 (2006.01)
C12N 1/00 (2006.01)
C12N 1/20 (2006.01)

(52) U.S. Cl. .................... 435/69.1; 435/243; 435/252.8
(58) Field of Classification Search ................ 435/69.1, 435/243, 252.8
See application file for complete search history.

(56) References Cited

U.S. PATENT DOCUMENTS 3,640,827 A * 2/1972 Lutz .................. 252/8.55
4,727,031 A * 2/1988 Brown et al. .............. 435/244

FOREIGN PATENT DOCUMENTS

CA 2078054 9/1992
DE 290212 A5 7/1988

OTHER PUBLICATIONS

Sambrook et al 1989 Molecular Cloning, A Laboratory Manual, CSHL, CSH, NY pp. 1.21–1.25.*
Zaika et al 1993 J Food Prot 56(7):577–580.*
Yee and Blanch, "Defined Media Optimization for Growth of Recombinant *Escherichia coli* X90", *Biotechnology and Bioengineering*, 41: 221–230 (1993).
Thompson et al., "Control of Ammonium Concentration in *Escherichia coli* Fermentations", *Biotechnology and Bioengineering*, 27: 818–824 (1985).
Neidhardt et al., "Culture Medium for Enterobacteria," *Journal of Bacteriology*, 119: 736–747 (1974).
Pirt, S.J., *Principles of Microbe and Cell Cultivation*, p. 134 (1975).
Majewski and Domach, "Simple Constrained–Optimization View of Acetate Overflow in *Escherichia coli*", *Biotechnology and Bioengineering*, 35: 732–738 (1990).
Corbridge, D.E.C., *Phosphorous: An Outline of its Chemistry, Biochemistry and Technology*, Fourth Edition, Chapter 3, pp. 277–285 (1990).
Roa and Torriani, "Utilization by *Escherichia coli* of a High–Molecular–Weight, Linear Polyphosphate: Roles of Phosphatases and Pore Proteins", *Journal of Bacteriology*, 170: 5216–5223 (1988).
Zabriskie and Arcuri, "Factors Influencing Productivity of Fermentations Employing Recombinant Microorganisms", *Enzyme Microb. Technol.*, 1986, vol. 8, Dec., pp. 706–717.
Gouesbet et al., "Osmotic Repression of Anaerobic Metabolic Systems in *Escherichia coli*", *Journal of Bacteriology*, 175, No. 1, Jan. 1993, p. 214–221.
Ryan and Parulekar, "Recombinant Protein Excretion in *Escherichia coli* JM103[pUC8]: Effects of Plasmid Content, Ethylenediaminetetraacetate, and Phenethyl Alcohol on Cell Membrane Permeability", *Biotechnology and Bioengineering*, vol. 37: pp. 430–444 Mar. (1991).

* cited by examiner

*Primary Examiner*—Karen Cochrane Carlson
(74) *Attorney, Agent, or Firm*—Randolph N. Mohr

(57) ABSTRACT

The invention relates to the use of a phosphate glass as a phosphorus source in the media of high cell density bacterial fermentation processes in order to reduce metallophosphate precipitation reactions. The methods of the invention demonstrate a practical method for controlling levels of metallophosphate precipitation in both the nutrient media and the fermentor which also result in increased cell densities and are useful in a variety of high cell density bacterial fermentation processes.

12 Claims, 1 Drawing Sheet

Growth with Phosphate Glass Compared to Orthophosphate

○ Hexaphos
● Orthophosphate

US 7,118,884 B1

METHOD FOR CONTROLLING METALLOPHOSPHATE PRECIPITATION IN HIGH CELL DENSITY FERMENTATIONS

This application is a continuation, of application Ser. No. 08/235,573 filed Apr. 28, 1994 now abandoned which is hereby incorporated by reference.

BACKGROUND OF THE INVENTION

The present invention relates to a bacterial fermentation process for producing a recombinant protein wherein certain feed media nutrients are monitored and adjusted so as to control metallophosphate precipitation in the media. In particular, the invention is to a high cell density fermentation process comprising a method wherein certain polyphosphates and/or metaphosphates are used in the media to eliminate nutrient precipitation and increase cell density.

Advances in molecular biology and the exploitation of recombinant DNA procedures has made possible the production of significant quantities of foreign proteins in certain host cell systems. Recombinant proteins are produced in the host cell systems by transfecting the host cells with DNA coding for the protein of interest, and then growing the transfected host cells under conditions which allow for expression of the new recombinant protein. Certain bacterial host cell systems can be used to produce large quantities of recombinant proteins which are normally available in limited quantities from natural sources.

The procaryote *Escherichia coli* is a bacterium which has been studied extensively. *E. coli.* is commonly selected for use in high expression host cell systems, in part, because *E. coli.* cells tend to be more amenable to production of extremely large quantities of recombinant protein. Host cell systems employing eucaryotic host cells and yeast host cells generally fail to produce recombinant protein in the tremendous quantities generated in the high expression host cell systems like *E. coli*. Moreover, development of high cell density fermentation processes has resulted in increased volumetric productivity of recombinant products in *E. coli*. Yee and Blanch, *Biotechnology and Bioengineering*, 41: 221–230 (1993).

The fermentation processes used to produce recombinant proteins in host cell systems, like the *E. coli*. system, are carried out in finite physical containers (i.e. fermentors, reactors). Stirred tanks represent the most popular geometry of fermentors, although an increasing number of other physically shaped vessels are being developed. Modes of fermentor operation may fall into any of the following categories: (1) discontinuous operation (batch process), (2) continuous operation, or (3) various types of semi-continuous operations such as the fed-batch process.

Depending upon the mode of operation and host cell system being employed, a defined balanced batch and/or feed medium must be devised which will allow for cell growth and expression of the recombinant protein. The defined medium is termed "minimal" if it only contains the nutrients essential for growth. For the *E. coli* system, the minimal media must include a source of carbon, nitrogen, phosphorus, magnesium, and trace amounts of iron and calcium. Gunsalus and Stanter, *The Bacteria*, Vol. 1, Chapter 1 Academic Press Inc., N.Y. (1960). Most minimal media use glucose as a carbon source, ammonia as a,nitrogen source, and orthophosphate (e.g. $PO_4$) as the phosphorus source. The ideal nutrient media for cell growth would include the exact amount of each nutrient that is consumed during cell growth, such that no nutrients accumulate to inhibitory levels, nor do the cells become starved of any nutrients. Thompson et al., *Biotechnology and Bioengineering*, 27: 818–824 (1985). A theoretically balanced minimal nutrient medium for *E. coli* has been devised previously for use in low cell density shake-flakes (cell densities up to 1.5 g cell dry weight/liter). Neidhardt et al., *Journal of Bacteriology*, 119: 736–747 (1974).

In addition to the chemical composition of the media, the effects of several other environmental parameters such as pH, time, cultivation temperature, and partial pressure of dissolved oxygen must be carefully considered. For example, the optimal pH for growth in *E. coli* is pH=7.0. During the fermentation process, pH of the media may be altered due to consumption of ammonia, or microorganism synthesis of certain metabolic products, e.g., acetic acid and lactic acid. Since altered pH may be unfavorable for optimal cell growth, it is critical to maintain the medium at a certain pH and this can be achieved by acid and base addition. The pH and other process parameters can be monitored manually or by automatic devices.

High cell density fermentations (i.e., those which achieve cell densities >20 g cell dry weight/liter) must employ a concentrated media. Operators performing high cell density fermentations have found that when working with concentrated nutrient medias, precipitates form when the solution containing the phosphate is mixed with the solution containing the other nutrient components. The precipitates that form in the nutrient media involve precipitation of orthophosphates and include $NH_4MgPO_4$, $(Mg)_3(PO_4)_2$, and metallo-phosphates of the form $(Me)_n(PO_4)_m$ (where Me=Fe, Ca, Zn, Cu, Co). These compounds have very low solubilities in water. Dean, John A., *Lange's Handbook of Chemistry*, 12th edition, McGraw-Hill, New York, pages 7–12 (1979). The amount of precipitation can vary depending upon pH, glucose concentration, and concentration of the media components.

Precipitate formation can lead to a number of problems in feed medium and in the fermentor. For example, precipitates in the feed medium can lead to a non-homogeneous feed supply (due to settling of precipitate in feed vessels or supply lines), and starvation of the cells for critical nutrients that are no longer soluble. The precipitates can also abrade feed pumps and piping and possibly clog the feed lines altogether.

In the fermentor, precipitation will occur if the media is not perfectly balanced for cell growth. Precipitation in the fermentor can cause clogging of the air sparger in the fermentor, lead to nonhomogeneous mixing (i.e. precipitate settles in lower levels of the fermentor) and reduce the availability of soluble nutrients to the cells. The concentration of nutrients available to the cells becomes dependent on the rate of nutrient loss due to precipitate formation compared to the rate of nutrient uptake by the cells. These effects can be compounded by the automatic addition of acid and base for pH control. All of these conditions reduce the reproducibility of the fermentation process. Furthermore, the presence of precipitates can impact protein purification operations and force the use of extra purification process steps in order to separate the precipitate from the product.

In the commercial setting, in order for the fermentation process to be practical, the precipitation problem must be alleviated. One suggested way to prevent nutrient precipitation in minimal medium is the addition of EDTA and citrate in order to chelate metal ions in the nutrient media. Pirt, S. J., *Principles of Microbe and Cell Cultivation*, page 134 (1975). However, the need to add chelating agents is not desirable because the agents are not metabolized. Consequently, they accumulate and increase the osmolarity of the cellular environment. High osmolarity has a detrimental effect on cellular metabolism. Gouesbet et al., *Journal of Bacteriology*, 175: 214–221 (1993). High concentrations of chelating agents can also damage cell membranes. Ryan et al., *Biotechnology and Bioengineering*, 37: 430–444 (1991).

In German Patent Application No. 290,212 A5 (filed Jul. 28, 1988), Riesenberg et al. describe a procedure for the preparation of a glucose minimal medium for use in mass culture fermentation of *E. coli* for obtaining recombinant DNA products. The minimal media described by Riesenberg et al. was designed to overcome the heavy precipitation problems normally encountered when working with such medias. The media described in the application utilizes orthophosphates as the phosphorus source and does not completely eliminate nutrient precipitation; but rather, is said to exhibit only low turbulence due to light precipitate formation.

Aside from the discussion above, nothing can be drawn from the literature concerning preparation of medias for high cell density fermentations which effectively eliminate the nutrient precipitation problem. A need still exists for a method for reducing precipitation in a batch and/or feed media which contains no precipitation when all components are mixed (mixed at neutral pH for *E. coli.*), and which assures that no precipitate will form in the fermentor during processing. The present invention provides such a method by using a sodium phosphate glass as the source of phosphorus in the concentrated nutrient media. Unlike the methods suggested in the cited references above, the methods of the present invention provide the triple advantage of: (1) allowing for the design of a concentrated, completely balanced batch and/or feed media containing no precipitate; (2) being capable of being metabolized by *E. coli*; and (3) allowing for increased cell density and growth rates. The practical methods of the present invention are useful in a variety of bacterial fermentations, especially high cell density fermentation processes.

SUMMARY OF THE INVENTION

The present invention relates to a bacterial fermentation process for producing a recombinant protein wherein certain feed media nutrients are monitored and adjusted so as to control metallophosphate precipitation during the process. In particular, the invention is to a high cell density fermentation process comprising a method wherein the concentrated nutrient solution uses sodium phosphate glass as the phosphorus source. Surprisingly, this method eliminates precipitate formation in the medias and results in increased cell densities at standard conditions.

DETAILED DESCRIPTION

Figure 1:
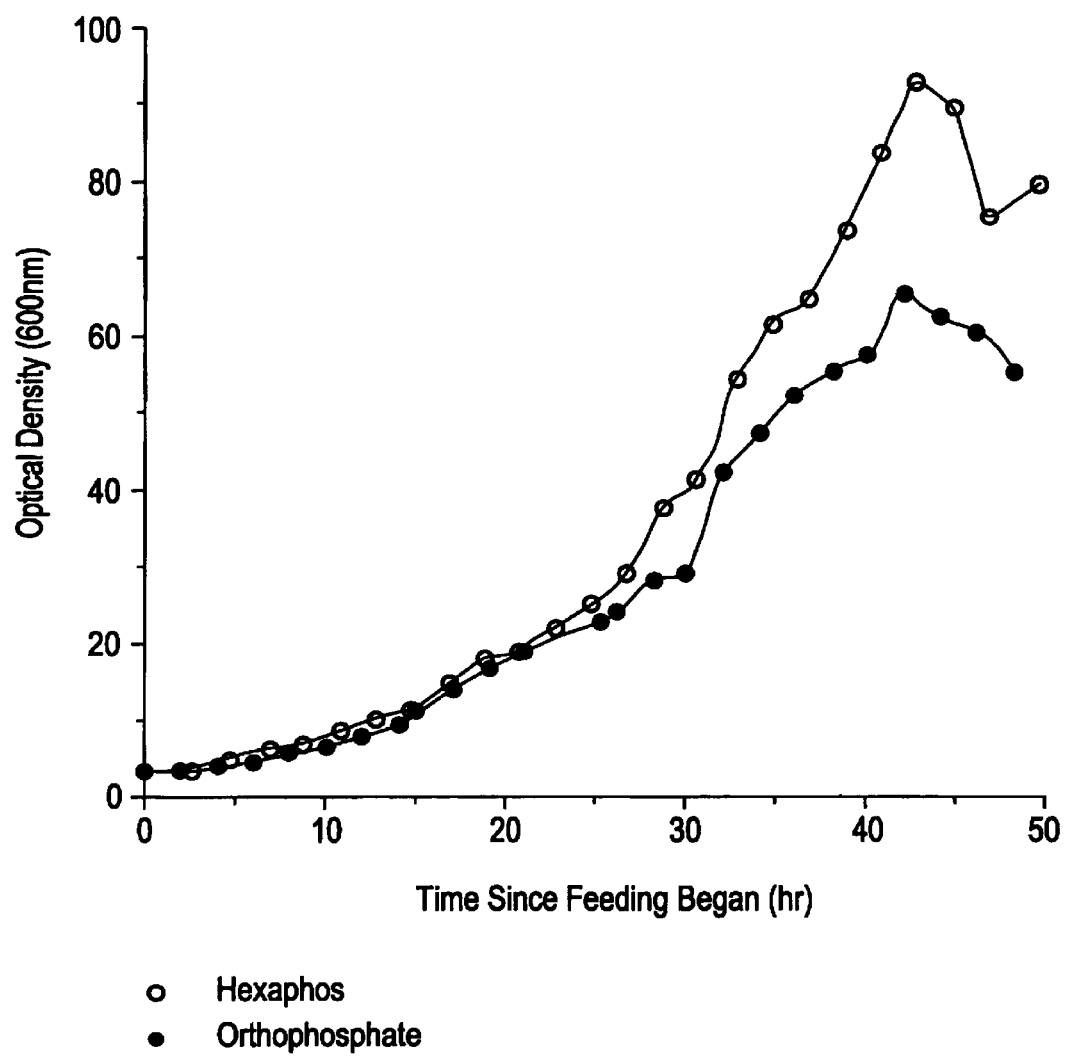
FIG. 1 shows cell density profiles from Run C (●-●) and Run D (○-○) demonstrating that use of a phosphate glass as the phosphorus source in the medias led to an increase in cell density over that obtained using orthophosphate as the phosphorus source. Cell density was measured using a Perkin-Elmer M35 Spectrophotometer and $OD_{600}$ was plotted against time.

The methods by which certain feed media nutrients are monitored and adjusted so as to control metallophosphate precipitation during the fermentation process are described in more detail in the discussion below and are illustrated by the examples provided below. The examples demonstrate that alternative phosphorus sources can be utilized in high cell density fermentations to eliminate nutrient precipitation. The results were surprising in that high cell density batch and fed-batch fermentations using a glassy sodium phosphate as the phosphorus source in the concentrated batch and/or feed media eliminated metallophosphate precipitation in the medias and resulted in increased cell densities in the fermentations.

The fermentation processes involved in the production of recombinant proteins will use a mode of operation which falls within one of the following categories: (1) discontinuous (batch process) operation, (2) continuous operation, and (3) semi-continuous (fed-batch) operation. A batch process is characterized by inoculation of the sterile culture medium (batch medium) with microorganisms at the start of the process, cultivated for a specific reaction period. During cultivation, cell concentrations, substrate concentrations (C-source, nutrient salts, vitamins, etc.) and product concentrations change. Good mixing ensures that there are no significant local differences in composition or temperature of the reaction mixture. The reaction is non-stationary and cells are grown until the growth limiting substrate (generally the carbon source) has been consumed.

Continuous operation is characterized in that fresh culture medium (feed medium) is added continuously to the fermentor and spent media and cells are drawn continuously from the fermentor at the same rate. In a continuous operation, growth rate is determined by the rate of medium addition, and the growth yield is determined by the concentration of the growth limiting substrate (i.e. carbon source). All reaction variables and control parameters remain constant in time and therefore a time-constant state is established in the fermentor followed by constant productivity and output.

Semi-continuous operation can be regarded as a combination of batch and continuous operation. The fermentation is started off as a batch process and when the growth limiting substrate has been consumed, a continuous feed medium containing glucose and minerals is added in a specified manner (fed-batch). In other words, this operation employs both a batch medium and a feed medium to achieve cell growth and efficient production of the desired protein. No cells are added or taken away during the cultivation period and therefore the fermentor operates batchwise as far as the microorganisms are concerned. While the present invention can be utilized in a variety of processes, including those mentioned above, a preferred utilization is in conjunction with a fed-batch process.

In each of the above processes, cell growth and product accumulation can be monitored indirectly by taking advantage of a correlation between metabolite formation and some other variable, such as medium pH, optical density, color, and titrable acidity. For example, optical density provides an indication of the accumulation of insoluble cell particles and can be monitored on-stream using a micro-OD unit coupled to a display device or a recorder, or off-line by sampling. Optical density readings at 600 nanometers ($OD_{600}$) are used as a means of determining dry cell weight.

High cell density fermentations are generally described as those processes which result in a yield >20 g cell dry weight/liter ($OD_{600}$>30). All high cell density fermentation processes employ a concentrated nutrient media that is gradually metered into the fermentor in a "fed-batch" process. A concentrated nutrient feed media is required for high cell density processes in order to minimize the dilution of the fermentor contents during feeding. A fed-batch process is required because it allows the operator to control the carbon source feeding, which is important because if the cells are exposed to concentrations of the carbon source high enough to generate high cell densities, the cells will produce so much of the inhibitory biproduct, acetate, that growth will stop. Majewski and Domach, *Biotechnology and Bioengineering*, 35: 732–738 (1990).

Standard reaction conditions for the fermentation processes used to produce recombinant proteins generally involve maintenance of pH at about 5.0 to 8.0 and cultivation temperatures ranging from 20° to 50° C. for *E. coli*. In the present invention, a preferred embodiment which utilizes *E. coli*. as the host system will have an optimal pH of about 7.0 and optimal cultivation temperature of about 37° C.

The standard nutrient media components in these fermentation processes generally include a source of energy, carbon, nitrogen, phosphorus, magnesium, and trace amounts of iron and calcium. In addition, the media may contain growth factors (such as vitamins and amino acids), inorganic salts, and any other precursors essential to product formation. The elemental composition of the microorganism under consideration can be used to calculate the proportion of each component required to support cell growth. The component concentrations will vary depending upon whether the process is a low cell density or high cell density process. For example, the glucose concentrations in low cell density batch fermentation processes range from 1–5 g/L, while high cell density batch processes use glucose concentrations ranging from 45 g/L to 75 g/L.

Contemplated for use in the practice of this invention as a phosphate source in the medias are a wide range of phosphate glasses. Phosphate glasses are linear polyphosphates having relatively specialized applications. For a general discussion of linear polyphosphates, including phosphate glasses, see Corbridge, D.E.C., *Phosphorus: An Outline of its Chemistry, Biochemistry and Technology*, Fourth Edition, Chapter 3, pages 210–302 (1990). Phosphate glasses can be prepared over a wide range of composition and consist mainly of a mixture of cations and discrete polyphosphate chains. The glasses formed with $Na^+$ cations have been examined most thoroughly, and exist in a continuous series, stable at normal temperatures, from the composition $P_2O_5$ up to $5Na_2O.100P_2O_5$. Phosphate glasses are formed by condensation of orthophosphate anions, i.e. heating $NaH_2PO_4$ to ~650° C. and quenching. A typical glass from a quenched melt at 650° C. and water vapor pressure of 55 torr has a mean chain length of $\tilde{n}=60$ $PO_4$ tetrahedra.

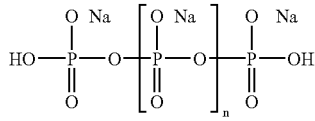

Glassy varieties of sodium polyphosphate are commercially available. These are manufactured with various average chain lengths (e.g. $\tilde{n}=5$ to $\tilde{n}=200$).

In general, the polyphosphates useful in the methods of the present invention are sodium phosphate qlasses. In particular, sodium phosphate glasses having chain lengths ranging $\tilde{n}=2$ to about A =100, wherin the chain length is defined as $PO_4—(PO_3)_{\tilde{n}-PO4}$ and $\tilde{n}2$–100 and more preferably about $\tilde{n}=4$ to about $\tilde{n}=20$ are contemplated for use.

These phosphate glasses are useful in the present invention because: (1) their solubility properties are such that concentrated nutrient medias can be prepared with no resulting precipitation upon mixing; (2) host cell systems such as the *E. coli*. system, have the necessary pathways to metabolize the phosphate glasses; and (3) because there is no precipitation, all nutrients are fully available for consumption, thereby resulting in increased cell densities and growth rates. In a preferred embodiment, a glassy sodium polyphosphate with a chain length of $\tilde{n}=11$ is used as the phosphorus source.

The present invention is useful in a process to produce a variety of recombinant proteins. Exemplary proteins contemplated are cytokines, including various hematopoietic factors such as G-CSF, SCF, EPO, GM-CSF, CSF-1, the interleukins such as IL-1 through IL-12, IGFs, M-CSF, TNF, or LIF. Other therapeutic proteins such as interferons (alpha-, beta-, gamma- or consensus interferons) and growth factors or hormones are also useful, such as human or other animal growth hormones (for example, porcine, or chicken growth hormone), FGF, KGF, EGF, and PDGF. Protease inhibitors, such as metalloproteinase inhibitors are contemplated (such as TIMP-1, TIMP-2, or other proteinase inhibitors). Nerve growth factors are also contemplated, such as BDNF and NT-3. Also contemplated are peptide portions of proteins having all or part of the primary structure of the parent protein and at least one of the biological properties of the parent protein.

In general, the KGF useful in the present invention has the sequence of human KGF, or closely related analogues thereof. Published PCT patent application WO 90/08771 describes the purification of KGF from the conditioned medium of a human embryonic fibroblast cell line, partial amino acid sequencing of the isolated polypeptide, cloning of the gene, and expression in bacterial cells (*E. coli*) to achieve recombinant, biologically active KGF.

In a preferred embodiment, the recombinant host cell used in the process is *E. coli*. *E. coli* is a preferred system because its genetics are well characterized, it allows for high cell densities, and it can be grown efficiently at normal conditions (e.g. pH and temperature).

Additional elements that provide preferred embodiments of the invention include complex nitrogen sources such as yeast extract and chemical digests of casein soy meal, meat, blood or cottonseed. As would be understood by a person having knowledge of the art, the invention encompasses methods of controlling metallophosphate precipitation having various combinations of these additional elements.

EXAMPLE 1

Balanced minimal nutrient feed medias, typical of those which would be employed to produce recombinant proteins in high cell density fermentations in *E. coli*. were prepared using alternative phosphate sources. A "standard" batch minimal media (designed Media A) using orthophosphate as the phosphorus source was compared to a media (designated Media B) which utilized Hexaphos™, a glassy sodium polyphosphate with a chain length of $\tilde{n}=11$ and supplied by FMC Corp., as the phosphorus source.

Media A contained 45 g/L glucose, 3 g/L yeast extract, 1 g/L $(NH_4)_2SO_4$, 4 g/L $K_2HPO_4$, 4.56 g/L $KH_2PO_4$, 0.71 g/L $MgSO_4.7H_2O$, 0.74 g/L KCl, 4.0 mL/L of trace metal solution A (27 g/L of $FeCl_3.6H_2O$, 2.0 g/L of $ZnCl_2.4H_2O$, 2.0 g/L of $CoCl_2.6H_2O$, 2.0 g/L $MnMoO_4.2H_2O$, 1.0 g/L of $CaCl_2.2H_2O$, 1.9 g/L of $CuSO_4.5H_2O$, 0.5 g/L of $H_3BO_3$, 1.6 g/L of $MnCl_2.4H_2O$, 73.5 g/L of sodium citrate.$H_2O$) and 4 mL/L of vitamin solution A (0.06 g/L biotin, 0.04 g/L folic acid, 1.4 g/L pyridoxine.HCl, 0.42 g/L riboflavin, 5.4 g/L pantothenic acid, 6.1 g/L niacin). Media B was identical to Media A except that 3.33 g/L Hexaphos™ was used as the phosphate source instead of $K_2HPO_4$ and $KH_2PO_4$.

During sterilization of each of the medias, the glucose and magnesium sulfate are sterilized together, the trace metals solution A is sterilized separately, and the other media components (including the orthophosphate) are sterilized separately. This is done in order to prevent undesirable side reactions. For Media B, the Hexaphos™ is also sterilized separately. With Media A, when all of the sterilized media components are mixed together, the resulting solution turned cloudy. The cloudiness was attributed to the occurrence of precipitation reactions. However, Media B remained transparent upon mixing.

The weight of the resulting precipitate was measured by taking 10 mL samples of the media and filtering through two 0.2 μm pore size nylon filters (Nalgene, 215-4020) in a filter holder (Nalgene, 300-4100). The second filter in line was used to estimate the mass increase due to soluble solids which are trapped within the membrane. The filters were air dried for several hours and then completely dried in a Labware 9000 Microwave drying oven with weight scale. The Labware 9000 was used for determining the dry weight of the filters before and after the sample was applied. The results are summarized in Table 1 below.

TABLE 1

| Media | Weight of precipitate |
|-------|----------------------|
| A | 0.20 grams/liter |
| B | Not Detectable |

EXAMPLE 2

High cell density fed-batch fermentations designed to produce recombinant KGF in *E. coli*. were performed in order to compare the use of a phosphate glass versus orthophosphate as the phosphorus source in the batch media and the concentrated nutrient feed media. Effects on metallophosphate precipitation levels in the medias as well as overall cell density were determined. A "standard" fed-batch minimal media run (designated Run C) using orthophosphate as the phosphorus source was compared to a run (designated Run D) which utilized Hexaphos™ as the phosphorus source.

For Run C, the batch medium contained 5 g/L glucose, 1.68 g/L $(NH_4)_2SO_4$, 0.05 g/L $K_2SO_4$, 0.36 g/L $NaH_2PO_4.H_2O$, 0.136 g/L $MgSO_4.7H_2O$, 0.008 g/L KCl, 0.78 mL/L of trace metal solution A (27 g/L of $FeCl_3.6H_2O$, 2.0 g/L of $ZnCl_2.4H_2O$, 2.0 g/L of $CoCl_2.6H_2O$, 2.0 g/L $MnMoO_4.2H_2O$, 1.0 g/L of $CaCl_2.2H_2O$, 1.9 g/L of $CuSO_4.5H_2O$, 0.5 g/L of $H_3BO_3$, 1.6 g/L of $MnCl_2.4H_2O$, 73.5 g/L of sodium citrate.$H_2O$). Run D was identical to Run C except that .28 g/L Hexaphos™ was used in place of $NaH_2PO_4.H_2O$.

For Run C, the feed medium contained 651.5 g/L glucose, 6.52 g/L $K_2SO_4$, 46.91 g/L $NaH_2PO_4.H_2O$, 17.69 g/L $MgSO_4.7H_2O$, 1.08 g/L KCl and 102 mL/L of the trace metal solution A. The feed medium Run D was identical to that of Run C except that 37.2 g/L Hexaphos™ was used instead of $NaH_2PO_4.H_2O$. For each run, the pH of the feed medium was adjusted to 7.0 by adding 36 mL/L of 40% v/v NaOH solution.

As was the case with the balanced minimal nutrient feed medias of Example 1, use of orthophosphate as the phosphorus source resulted in the formation of precipitation upon mixing the sterilized media components. Use of Hexaphos™, on the other hand, resulted in no such precipitation. The weight of the resulting precipitate was measured using the procedure described in Example 1 and the results are summarized in Table 2 below.

TABLE 2

| Run | Weight of precipitate |
|-----|----------------------|
| C | 0.33 grams/liter |
| D | Not Detectable |

Cell densities for Runs C and D were also monitored. In each run, cells are initially grown batchwise in the batch medium. After the glucose has been consumed, a continuous feed using the feed medium is started. During this fed-batch portion of the fermentation, the feed rate is increased at two hour intervals according to the cell density. In Run C, the growth rate started at 0.08 $h^{-1}$ and declined to 0.04 $h^{-1}$ 42 hours after feeding began when the cell density of OD 65 was achieved. The OD then declined. In Run D, the fermentation grew at a steady rate of 0.09 $h^{-1}$ for 43 hours when a cell density of OD 92 was achieved. The OD then declined (see FIG. 1). The result was a final cell density of 61 g cell dry weight/liter for Run D compared to only 43 g cell dry weight/liter for Run C. As a result, Run D produced 180 mgs/liter KGF while Run C produced 120 mgs/liter KGF.

EXAMPLE 3

Several polyphosphates chain lengths ranging $\tilde{n}=2$ to $\tilde{n}=19$), wherin the chain length is defined as $PO_4$—$(PO_3)_{\tilde{n}}$—$PO_4$ and $\tilde{n}=2–1000$, other than Hexaphos™ were utilized as a phosphorus source in media preparations typical of those utilized for high cell density fermentations in *E. coli*. Several medias containing glucose:phosphorus and glucose::magnesium ratios typical of those necessary in high cell density fermentations were formulated by mixing a concentrated stock solution of glucose/magnesium sulfate (containing 888 g glucose/L) with concentrated solutions of different phosphorus-containing compounds and water. The pH of each resulting solution was adjusted to pH=7.0 using either 40% NaOH or 30% HCl.

Visual examinations of each solution were performed daily for five days to check for precipitate formation. Results are summarized in Table 3 below. The, results show that use of Hexaphos™ as the phosphorus source in the media allows for use of glucose concentrations as high as 800 g/L without the incidence of precipitation. Use of Glass H™, a glassy sodium polyphosphate with a chain length of $\tilde{n}=19$, and Sodaphos™, a glassy sodium polyphosphate with a chain length of $\tilde{n}=4$, allows for use of glucose concentrations as high as 600 g/L. Use of orthophosphate, on the other hand, allows for a maximum glucose concentration of only 462 g/L.

TABLE 3

| Phosphorus Source | Chain Length ($\tilde{n}$) | Days For Precipitation To Form | | | | |
|---|---|---|---|---|---|---|
| | | 800 g/L Glucose | 600 g/L Glucose | 400 g/L Glucose | 200 g/L Glucose | 100 g/L Glucose |
| Glass H ™ | 19 | 2 | None | None | None | None |
| Hexaphos ™ | 11 | None | None | None | None | None |
| Sodaphos ™ | 4 | 2 | None | None | None | None |
| Tripoly-phosphate | 1 | 1 | 1 | 1 | None | None |
| Ortho-phosphate | N/A | N/A | 0* | None | None | None |

*Maximum glucose concentration obtainable is 462 g/L.

chain length is defined as $PO_4$—$(PO_3)_{\tilde{n}}$—$PO_4$ and $\tilde{n}=2$–100. These results demonstrate that a variety of glassy sodium polyphosphates are effective in eliminating nutrient precipitation in the concentrated medias used for the production of recombinant proteins in the high cell density fermentations.

The results presented herein demonstrate a practical method for controlling metallophosphate precipitation reactions in the media used in high cell density bacterial fermentation processes, and will provide for improved cell growth and protein production in a variety of high cell density bacterial fermentation processes.

What is claimed is:

1. A method for reducing precipitation in a bacterial fermentation process for producing a recombinant protein comprising inclusion of phosphate glasses as a phosphorus source in the nutrient media during production of said protein; wherein said process is a high cell density fermentation process.

2. The method of claim 1 wherein said phosphate glasses are selected from the group consisting of sodium phosphate glasses having chain lengths ranging from about $\tilde{n}=2$ to about $\tilde{n}=100$, wherein the chain length is defined as $PO_4$—$(PO_3)_{\tilde{n}}$—$PO_4$.

3. The method of claim 2 wherein said sodium phosphate glass has a chain length of about $\tilde{n}=4$ to about $\tilde{n}=20$.

4. The method of claim 3 wherein said sodium phosphate glass has a chain length of $\tilde{n}=11$.

5. The method of claim 1 wherein said high cell density fermentation is selected from the group consisting of a batch fermentation, a continuous fermentation, and a fed-batch fermentation.

6. A method for increasing cell density in a bacterial fermentation process for producing a recombinant protein comprising inclusion of phosphate glasses as the phosphorus source in the nutrient media during production of said protein; wherein said process is a high cell density fermentation process.

7. The method of claim 6 wherein said phosphate glasses are selected from the group consisting of sodium phosphate glasses having chain lengths ranging from about $\tilde{n}=2$ to about $\tilde{n}=100$, wherein the chain length is defined as $PO_4$—$(PO_3)_{\tilde{n}}$—$PO_4$.

8. The method of claim 7 wherein said sodium phosphate glass has a chain length of about $\tilde{n}=4$ to about $\tilde{n}=20$.

9. The method of claim 8 wherein said sodium phosphate glass has a chain length of $\tilde{n}=11$.

10. The method of claim 6 wherein said high cell density fermentation is selected from the group consisting of a batch fermentation, a continuous fermentation, and a fed-batch fermentation.

11. A method for reducing precipitation in a high cell density fermentation process for producing a recombinant protein in *E. coli*, comprising inclusion of a phosphate glass having a chain length of about $\tilde{n}=4$ to about $\tilde{n}=20$, wherein the chain length is defined as $PO_4$—$(PO_3)_{\tilde{n}}$—$PO_4$, as a phosphorus source in the nutrient media during production of said protein.

12. The method of claim 11 wherein said phosphate glass has a chain length of about $\tilde{n}=11$.

* * * * *